(12) United States Patent
Chaudhary et al.

(10) Patent No.: US 8,268,367 B2
(45) Date of Patent: Sep. 18, 2012

(54) TOPICAL HERBAL FORMULATION FOR TREATMENT OF ACNE AND SKIN DISORDERS

(75) Inventors: Manu Chaudhary, Panchkula (IN); Vijay Naithani, Panchkula (IN)

(73) Assignee: Sunev Pharma Solution Limited, Haryana (IN)

( * ) Notice: Subject to any disclaimer, the term of this patent is extended or adjusted under 35 U.S.C. 154(b) by 0 days.

(21) Appl. No.: 13/139,716

(22) PCT Filed: Dec. 30, 2009

(86) PCT No.: PCT/IN2009/000754
§ 371 (c)(1),
(2), (4) Date: Jun. 14, 2011

(87) PCT Pub. No.: WO2010/076812
PCT Pub. Date: Jul. 8, 2010

(65) Prior Publication Data
US 2011/0262499 A1   Oct. 27, 2011

(30) Foreign Application Priority Data
Dec. 31, 2008   (IN) .......................... 2975/DEL/2008

(51) Int. Cl.
*A61K 36/00* (2006.01)
*A61K 36/73* (2006.01)
*A61K 36/752* (2006.01)
*A61K 36/53* (2006.01)
*A61K 36/534* (2006.01)
*A61K 9/00* (2006.01)

(52) U.S. Cl. ........ 424/725; 424/400; 424/736; 424/765; 424/747

(58) Field of Classification Search ........................ None
See application file for complete search history.

(56) References Cited

U.S. PATENT DOCUMENTS

| | | |
|---|---|---|
| 6,368,639 B1 | 4/2002 | Farooqi et al. |
| 2004/0019112 A1 | 1/2004 | Maley |
| 2007/0237837 A1* | 10/2007 | Pipko et al. ................... 424/717 |
| 2008/0254150 A1 | 10/2008 | Rheins et al. |

FOREIGN PATENT DOCUMENTS

| | | | |
|---|---|---|---|
| JP | 2008/031049 | | 2/2008 |
| WO | WO 2005/027872 | * | 3/2005 |

* cited by examiner

*Primary Examiner* — Qiuwen Mi
(74) *Attorney, Agent, or Firm* — Dennison, Schultz & MacDonald (57) ABSTRACT

The present invention provides novel herbal nano emulsion based formulations comprising a combination of lemon juice and/or rose water as therapeutically active aqueous phase entrapped in oil phase selected from one or more essential oils and process for the preparation of the same in pharmaceutically acceptable dosage forms for topical treatment of acne and other skin disorder like eczema, psoriasis, aging scaring and the like with increased efficacy, improved percutaneous penetration, excellent thermodynamic stability ensuring long shelf life, low skin irritation and reservoir effect that promotes drug localization in the skin enabling controlled delivery of the said therapeutic agents.

9 Claims, 2 Drawing Sheets

Fig: 1 Graph showing Zeta potential of XLP07 (Product of Current invention)

Fig:2 Graph Particle size distribution and Poly Dispersity Index(PDI) of XLP07

Fig3: Graph showing Comparative MDA activity in Acne Induced Model in rat

Fig:4 Graph Indicating Comparative Myloperoxidase (MPO) activity in Acne induced Model in rats G I : control untreated G II: Clearasil Treated G III : XLP07 Treated

TOPICAL HERBAL FORMULATION FOR TREATMENT OF ACNE AND SKIN DISORDERS

This application is a 371 of PCT/IN2009/000754 filed on Dec. 30, 2009, which is incorporated herein by reference.

FIELD OF INVENTION

The present invention relates to the field of topical herbal formulations based on nano technology having therapeutic properties. More specifically it relates to nano-emulsion based topical synergistic herbal formulations which are effective against acne and other skin disorder, and process for the preparation of the same in pharmaceutical acceptable dosage forms. Further more specifically, the present invention is concerned with the prophylactic and therapeutic topical treatment of skin disorders of all types of acne, eczema, psoriasis, aging, scaring and the like. Even more specifically, the present invention is concerned with the topical treatment having improved penetration, long acting, low irritation, better efficacy, synergistic bacteriostatic activity and controlled delivery of therapeutic agents.

BACKGROUND OF THE INVENTION

Acne is the most common cutaneous disorder of multifactorial origin with a prevalence of 70-85% in adolescents. According to the statistics, nearly 85% of people aged 12-25 years, approximately 8% of adults aged 25-34 years, and 3% of adults aged 35-44 years experience some degree of acne [Befd W F, *J Am Acad Dermatol* 1995; 32:552-556]. In the US alone, between 40 and 50 million people are estimated to be affected by some form of acne, with approximately 17 million having clinical acne [Thiboutot D, *Arch Fam Med;* 2000; 9:179-187]. Although acne and other skin disorders such as eczema, psoriasis, aging, scaring and the like are not life-threatening diseases, but it has significant physical and psychological ramifications such as permanent scarring, poor self-image, social inhibition, depression, anxiety and suicidal tendency [Gupta et al, *Br J Dermattol;* 1998; 78:451-456]. Therefore, these may be regarded as serious medical disorders. Moreover, there is increasing evidence that hereditary factors and stress play an important but indirect role in acne and the said skin orders. Recently, smoking have also been found to be associated with these diseases. Topical therapy is inevitable in acne treatment and is mainly indicated in the mild to moderate acne. In more severe forms, a combined topical and systemic therapy is recommended [Date Et al, *Skin Pharmacol Physiol;* 2006; 19:2-16].

The available topical agents have a direct or indirect influence on the patho-genetic factors and are selected according to the predominant type of acne lesions. The therapeutic success in acne and related skin disorders are highly dependent on a regular application of the topical agents over a prolonged period of time. However, disadvantages associated with the commonly used topical agents considerably affect the patient compliance and obstruct the treatment. Currently, available treatment for acne and related skin disorders is mostly based on antibiotics and retinoids. The uses of antibiotics have a lot of limitations due to development of resistance by bacteria. Retinoids are highly teratogenic.

Most of the anti-acne agents are virtually insoluble in water, and thus difficult to incorporate into aqueous systems. Thus the strategy of combining many anti-acne actives in one composition to treat acne is not new, for example, such a combination is disclosed in U.S. Pat. No. 5,976,565 as a patch. Another combination is described in U.S. Pat. No. 4,428,933, wherein a combination of oats, sulfur powder, zinc gluconate, mustard seed, boric acid powder, brewer's yeast, hydrogen peroxide, iso-propyl alcohol, water, methyl p. hydroxy benzoate, and egg yolks are described for treating acne. Patent WO/2003/030816 discuss about anti acne formulation derived from natural products particularly polysacchrides from red algae.

The use of salicylic acid in the treatment of common or teen acne is known. For example, U.S. Pat. No. 4,665,063 describes the use of topically applied aspirin (acetyl salicylic acid) for treating common acne; and U.S. Pat. No. 4,891,227 describes the use of pads for applying anti-acne products containing salicylic acid for oily skin. These patents describe state-of-art compositions which emphasize aggressive chemical and physical treatment suitable for teen acne, without addressing the suitability for adult acne and/or the need for mildness.

U.S. Pat. No. 4,800,197 describes a combination of salicylic acid and an anionic taurate surfactant, specifically sodium methyl cocoyl taurate or sodium methyl oleoyl taurate. U.S. Pat. No. 5,296,476 describes the specific use of salicylic acid in combination with calcium citrate. Again, these treatment modalities are designed for aggressive, physical cleansing, which assumes that the individual indicators are normal, young and oily skin.

Currently available forms of salicylic acid tend to aggravate the relatively dry adult acne, and they are particularly unsuitable for those with sensitive skin conditions such as irritant folliculitis. Known salicylic acid preparations are also poorly tolerated in patients suffering from acne complexed with rosacea.

Therefore, an alternative treatment for acne and other skin disorders must be studied and developed. This creates a great interest towards the possible effect of natural substances on antibacterial, anti-inflammatory, oxidative stress reducing action in these diseases. Novel drug delivery strategies have also been instrumental in optimizing efficacy of therapeutic agents by either modulating their physico-chemical and bio-pharmaceutical properties or minimizing/eliminating the side effects associated with them, reducing treatment time thus offering better patient compliance.

This is well documented in prior art that essential oils are valuable tool for skin care. Essential oils plays an very important role in acne treatment because they are soluble through lipids in the skin and are easily absorbed and also because of their ability to dissolve sebum, kill bacteria, and preserve the acid mantle of the skin. Used full strength or diluted with a carrier oil, essential oils can be applied topically to relieve mild to moderate acne. Some essential oils commonly used for acne treatment are Rosewood Oil, Jojoba Oil, Bergamot Oil, Clove Oil, Lavender Oil, Tea Tree Oil, Tulsi oil, Rosemary oil, Lavender oil, Mentha oil etc.

Tea tree oil is an excellent antibacterial treatment making it an excellent acne fighter as well as a general purpose wound cleaner. Biju et al. [Pharmazie 2005; 60: 208-211] have developed micro-emulsions using tea tree oil, using isopropyl myristate, Polysorbate 80, glycerin with water and U.S. Pat. No. 6,464,989 B2 discloses tea tree oil emulsion but not with aqueous phase using rose water and lemon juice as therapeutic agents entrapped in oil phase of one or more essential oils as used in the current invention.

Irritant folliculitis, caused by epithelial irritations, is another sensitive skin condition which manifests as erythematous papules and follicular pustules. Recurrent episodes of irritant folliculitis are sometimes misdiagnosed as common acne and treated with physical abrasives and exfoliants which traumatize and aggravate the original condition.

Acne is the most common cutaneous disorder of multifactorial origin with a prevalence of 70-85% in adolescents. According to the statistics, nearly 85% of people aged 12-25 years, approximately 8% of adults aged 25-34 years, and 3% of adults aged 35-44 years experience some degree of acne. Therefore, these may be regarded as a serious medical disorders and need an improved solution. Therefore, there is a dire need to develop such formulations which are effective to all skin types and have synergistic multiple effects, have good penetration, long acting to avoid repeated administration, non irritating and involves both aqueous and lipid phases in specific ratio to provide a cure for skin treatments to minimize the adverse effects and maximize the efficacy.

SUMMARY OF THE INVENTION

According to the present invention novel herbal nano-emulsion based formulations, their compositions and process of preparation are provided which are used for topical application, for the treatment and cure of all types of acne and other skin disorders including eczema, psoriasis, aging, scaring and the like. The herbal formulations comprise one or more essential oils in a particular weight ratio as oil phase and rose water and/or lemon juice in a particular ratio as aqueous phase which is medicated with at least one or more non ionic surfactants. The compositions exhibit remarkable synergistic efficacy in treating and curing acne and other skin disorders with improved percutaneous penetration, excellent thermodynamic stability ensuring long shelf life, low skin irritation and reservoir effect that promotes drug localization in the skin enabling controlled delivery of the therapeutic agents. The disclosed herbal formulations further can be used as a vehicle to carry any other lipophilic/lipophobic drugs for effective treatment of skin disorder.

OBJECTS OF THE INVENTION

It is an objective of the invention to provide novel herbal formulations for topical applications, for the treatment and cure of all types of acne and other skin disorders including eczema, psoriasis, aging scaring and the like.

Another objective of the present invention is to disclose herbal formulations with novel delivery system based on nano technology.

Yet another object of the invention is to combine rose water and/or lemon juice in specific ratio as therapeutically active aqueous phase of the said formulations.

Still another object of the invention is to stabilize aqueous phase by entrapping it in lipid phase consisting of one or more essential oils so as to make a stable, synergistic nano-emulsion for topical application.

Another object is to disclose compositions and method of manufacture of the said formulations.

Yet another objective is to provide herbal topical formulations which have improved percutaneous penetration, excellent thermodynamic stability ensuring long shelf life, low skin irritation, bacteriostatic/bactericidal activity and reservoir effect that promotes drug localization in the skin enabling controlled delivery of the therapeutic agents.

Yet another objective of present invention is to disclose herbal formulations which can be used as a vehicle or base to carry any other lipophilic/lipophobic drugs for effective treatment of skin disorders.

DETAILED DESCRIPTION OF THE PREFERRED EMBODIMENT

The present invention describes novel herbal formulations, their novel delivery mechanisms, compositions and process for the preparation of the same in pharmaceutical acceptable dosage forms for treatment of acne and other skin disorder including eczema, psoriasis, aging, scaring and the like.

The use of fresh lemon juice and rose water for treatment of acne is well established but the composition is not commercially available as a pharmaceutically acceptable dosage form because the combination is unstable for more than two to four hours at room temperature which limits the use of this combination and indicates towards the need of a stable formulation.

The concept behind the present invention is not only to overcome the stability problem of rose water & lemon juice combination for the treatment of acne and other skin disorders but also to provide technological advancements. Inventors could successfully stabilize the combination of rose water and/or lemon juice in specific ratio. This combination or the lemon juice alone can be used as a therapeutically active aqueous phase of the formulations by entrapping this aqueous phase into a lipid layer so as to form a controlled release form for topical application in a novel delivery system which is nano technology based i.e. nano-emulsion which further contributes synergistic effect of the one or more essential oils which are selected as oil phase for the said formulations. Thus invention not only provides a stabilized version of existing known prior art composition of rose water and/or lemon juice but also has a lot of technical advancements in terms of making it more effective, long acting with increased percutaneous penetration, low skin irritation and controlled delivery of the therapeutically active phytochemical agents by converting them into nano-emulsion with synergistic anti inflammatory, analgesic, bacteriostatic/bactericidal, anti oxidant, immuno modulatory action for topical application.

Novelty of the present Invention lies in the development of novel herbal formulations consisting of one or more therapeutically active components as aqueous phase which has strong antibacterial activity but poor stability; which is made stable by entrapping it in one or more essential oils used as oil phase and mixed in such a ratio so as to provide therapeutic synergy as well as formulation compatibility, thus making W/O nano-emulsions made of therapeutically active phytochemicals for the treatment of acne and other associated skin disorders. Due to increased interfacial surface and decreased surface tension topical delivery of nano emulsions are more effective and stable as compared to other macro emulsions or creams.

Inventive step of the present invention lies in selecting the specific components for novel delivery system, using the rose water and/or lemon juice as aqueous phase and stabilizing the therapeutically active phytochemicals present in said aqueous phase along with one or more essential oils in a specific ratio so as to provide a complete synergy to form nano-emulsion which enables sustained release of aqueous phase entrapped in oil phase and quick penetration into the skin due to reduction in particle size by formation of nano emulsion.

One of the embodiments of the current invention is to disclose the process for the preparation of such novel drug delivery system present as nano-emulsion for topical use.

Another embodiment of the invention is to provide herbal formulations with increased efficacy, improved percutaneous penetration, excellent thermodynamic stability ensuring long shelf life, low skin irritation and reservoir effect that promotes drug localization in the skin enabling controlled delivery of the therapeutic agents with synergistic anti inflammatory, analgesic, bacteriostatic/bactericidal, anti oxidant, immuno modulatory action for topical application.

Commercial applicability: The product have a very good commercial potential to cure a very large number of patients suffering from acne and other skin disorder including eczema, psoriasis, aging, scaring and the like.

Another embodiment of the invention, is to disclose compositions of the formulations composed of one or more essential oils in a particular ratio as oil phase and rose water and/or lemon juice in a particular ratio as aqueous phase with at least one or more non ionic surfactants and co surfactant.

Essential oils used in the formulations are selected from a group comprising Tea tree oil, Tulsi oil, Rosemary oil, Lavender oil, Rosewood Oil, Jojoba Oil, Bergamot Oil, Clove Oil, Mentha oil and the like. Because essential oils may be slightly drying to the skin when applied undiluted, it may be necessary to dilute them using a carrier oil to keep the skin hydrated. The addition of aqueous phase in place of carrier oil provided a diluent to the essential oils selected for the formulations in the current invention.

One of the preferred embodiment of the current invention contains one or more essential oils such as Tea tree oil, Tulsi oil, Rosemary oil, Lavender oil and Mentha oil in specific ratios. The selection was based on individual efficacy of these components for the said specific use. Acne sufferer's skin is very sensitive to tea tree oil which is generally used in concentration of 5-7%. However, in the current formulations inventors have used up to 15-36% Tea Tree oil successfully without causing skin irritation for the first time.

Aqueous phase selected for the nano-emulsions is medicated and consists of one or more therapeutically active phyto chemical components of herbal/natural origin instead of using water which is conventionally used as a preferred choice for aqueous phase in emulsions made of herbal/natural products. The said medicated therapeutically active components of aqueous phase consist of rose water and/or lemon juice in ratio of 1:1 or lemon juice alone. The phytochemicals present in said aqueous phase of rose water and/or lemon juice are not stable for more than 2 to 4 hours and thus posed a technical barrier of using these as therapeutically active components. The components were therefore, trapped inside lipid bi-layer of essential oils thus leading to preparation of macro emulsion. This emulsion had some inherent short comings as the preparation was skin irritating and sticky making the oil phase rancid. This further posed a challenge to overcome the problems, which was done by altering the ratios of essential oils used and using surfactants and co surfactants.

Surfactant used in the said formulations are non-ionic in nature and selected from a group comprising polyoxyethylene sorbitan fatty acid esters, Tweens such as Tween-80, Tween-20, polyethylene glycols, polyoxyethylene stearates, colloidal silicon dioxide, phosphates, sodium dodecyl sulfate, carboxy methyl cellulose calcium, carboxy-methyl cellulose sodium, methyl cellulose, hydroxyethyl cellulose, hydroxypropylcellulose, hydroxy-propylmethyl cellulose phthalate, micro-crystalline cellulose, magnesium aluminum silicate, tri-ethanolamine, polyvinyl alcohol, and polyvinylpyrrolidone (PVP) and the like. The ionic surfactants commonly used are of animal origin and have not been selected intentionally by the inventors. The co surfactant used are selected from a group comprising short and medium chain alcohols such as ethanol, methanol, iso propyl alcohol and the like. Formulations may additionally contain one or more softeners selected from a group comprising cedyl alcohol, emollients, cocoa butter, iso propyl myristate, iso propyl lanolate, lanolic acid, stearic acid and the like. Softeners are used to avoid any burning sensation or hardening of skins.

The active phyto chemicals in aqueous phase consist of Citric acid, ascorbic acid, Quercetin 3-O-rutinoside-7-O-glucoside, chrysoeriol 6,8-di-C-glucoside (stellarin-2), apigenin 6,8-di-C-glucoside (vicenin-2), eriodictyol 7-O-rutinoside, 6,8-di-C-glucosyl diosmetin, hesperetin 7-O-rutinoside, homoeriodictyol 7-O-rutinoside and diosmetin 7-O-rutinoside, Vitamin A, water soluble constituents of rose oil and the like and in essential oils consist of Terpinen-4-ol, γ-terpinene, α-terpinene, 1,8-Cineole, α-terpinolene, α-terpineol, α-pinene & p-cymene, Eugenol, Cinnamate, citronellol, geraniol, linalool, myrcene, pinene, ocimene, terpineol, methyl chavicol, citral, camphor, camphene, limonene, α-pinene, 1,8-cineol (eucalyptol) and camphor, camphene, limonene, borneol, verbenone, β-myrcene, β-pinene, Linalool, α-terpineol, γ-terpineol, Borneol, Iso-borneol, Terpinen-4-ol, Nerol, Lavandulol, Terpenes, Terpene esters, Linalyl acetate, Geranyl acetate, Neryl acetate, Octene-3-yl acetate, Lavandulyl acetate, Myrcene, α-pinene, β-pinene, Camphene, E-β-ocimene, Z-β-ocimene, β-phellandrene, Eucalyptol (1,8-cineol), β-caryophyllene, β-framesene, Germacrene, α-humulene, Ketones, camphor, Octanone, Cryptone, L-menthol, menthonene, menthone, alpha-pinene, a-1-limonene, carophyllene and cademene and the like.

The choice of surfactant, co-surfactant and softeners used in the formulations and their ratios, ranges may be altered by a person skilled in the art and the results may be gagged without departing from the spirit and scope of the present invention.

One of the preferred embodiments discloses use of 20±5% of tea tree oil, 5±5% of rose merry oil and 1±5% of mantha oil as oil phase making a total of 25±5% of essential oils as oil phase and 25±5% of freshly squeezed lemon juice mixed in equal amount as aqueous phase. The preferred surfactants used are non ionic long chain polymers and the ratio of Tween 20:Tween 80 is 88:12. The co surfactant used is preferably ethanol and the ratio without surfactant:co surfactant is 1.5:1 with HLB value of 16.7. The nano emulsion formulations made are energy efficient and are made as W/O type nano emulsion using ratio of oil:aqueous phase as 1:1. The formulation thus made has particle size of $\leq 0.5$ nano meter, zeta potential is $\leq -0.0326$ and poly dispersity index (PDI) is $\leq 0.169$. Negative Zeta potential and PDI<1 indicates the thermodynamic stability of nano emulsion.

Another preferred embodiment of the current invention disclose use of 18±5% Tea tree oil, 4±5% Tulsi oil, 2±5% Rosemary oil, 5±5% Lavender oil and 7±5% Mentha oil together as oil phase entrapping the 1:1 ratio of lemon juice: rose water mixture as aqueous phase where the ratio of oil phase:aqueous phase is 2:1, thus making a nano emulsion using Tween 20:Tween 80 in the ratio of 70:30, more specifically 80:20, further more specifically 88:12 along with ethanol as co surfactant where the ratio of surfactant:co surfactant is 1.2:1 with addition of 0.75 g Lanolin acid & 1.5 g Stearic acid as softening agents. The nano emulsion thus formed has particle size $\leq 5$ nm, zeta potential is $\leq -0.0500$ and poly dispersity index (PDI) is $\leq 0.200$.

Another embodiment of the current invention is to formulate a W/O type nano-emulsion in which ratio of water:oil is 1:1 to 1:2 which is thermodynamically stable and ensures long shelf life to the formulations. The particle size of said nano-emulsion range between 0.5 to 50 nm with PDI index between 0.100 to 0.200 and Zeta potential between $-0.0100$ to $-0.0500$, more preferably particle size is $\leq 5$ nm, PDI index is $\leq 0.200$ and Zeta potential is $\leq -0.0500$. The ratios of surfactant to co surfactant used in the formulations vary from 1.5:1 to 1:1.5. Nano emulsions thus made using one or more of phytochemicals comprise a medicated aqueous phase having strong antibacterial properties which is made stable by entrapping this aqueous phase into a lipid layer of essential oils so as to form a controlled release formulation having increased efficacy, improved percutaneous penetration, excellent thermodynamic stability ensuring long shelf life, low skin irritation and reservoir effect that promotes drug localization in the skin enabling controlled delivery of the therapeutic agents with synergistic anti inflammatory, analgesic, bacteriostatic/bactericidal, anti oxidant, immuno modulatory action for the prophylactic and therapeutic topical application used in the treatment and cure of all types of acne and other skin disorders including eczema, psoriasis, aging scaring and the like. The formulation thus made may also be used as a vehicle or base to carry any other lipophilic/lipophobic drugs for effective treatment of skin disorders.

Nano emulsions increase the rate of absorption, improves percutaneous penetration, eliminates variability in absorption, helps solublize lipophobic therapeutic agents/phyto chemicals, increases bioavailability, helps in rapid and efficient penetration of the active moiety, provides protection from hydrolysis and oxidation as drug in oil phase because such an emulsion is not exposed to attack by water and air, increases patient compliance and requires lesser amount of energy, thus making current invention technically advanced compared to other topical preparations detailed in prior art.

The process of preparation used for nano-emulsion as defined here in below includes following steps:

Step 1a.: Take Rose water and/or freshly squeezed Lemon juice in 1:1 ratio or lemon juice alone as aqueous phase and filter with 0.2 micron filter.

Step 1b.: Mix 30±7% of essential oils and 20±7% ml of aqueous phase and termed as (A).

Step 2a: Mix suitable surfactants in the ratio of 70:30, more specifically 80:20, further more specifically 88:12 and termed (B)

Step 2b: Emulsify (A) with the help of 28±5% suitable surfactant mixture (B)

Step 3a: Stir for 15 minutes, the resulting macro-emulsion obtained is milky in colour which is termed as (C).

Step 4: Take ethanol as co-surfactant separately termed as (D).

Step 5: Mix 20±5% of (D) into (C). The mixture obtained is termed as (E).

Step 6: Add suitable softeners after heating to the above mixture optionally depending upon formulation requirement.

Step 7: Use colloidal mill and filter the resultant nano emulsion with suitable filters and fill in suitable containers.

Nano-emulsion thus obtained has particle size of $\leq 5$ nano meter. Steps involved in formulation include but are not limited to the disclosures made here in above.

EXAMPLE 1

Formulation Trial 1: Each 100 ml Contains (XLP01)

| Name | Composition |
| --- | --- |
| Tea tree oil | 20.2 ml v/v |
| Tulsi oil | 8.2 ml v/v |
| Rosemary oil | 1.9 ml v/v |
| Lavender oil | 5.4 ml v/v |
| Rose water:Citrus juice in 1:1 ratio | 17.8 ml v/v |
| Surfactant 88% Tween 20 and 12% Tween 80 (Hydrophilic Lipophilic Balance = 16.7) | 25 ml |
| Co-surfactant 95% Ethanol | 21 ml |
| Softeners Lanolin & Stearic acid | q.s. |

EXAMPLE 2

Formulation Trial 2: Each 100 ml Contains (XLP02)

| Name | Composition |
| --- | --- |
| Tea tree oil | 23.5 ml v/v |
| Tulsi oil | 9.4 ml v/v |
| Rosemary oil | 2.8 ml v/v |
| Rose water:Citrus juice in 1:1 ratio | 17.8 ml v/v |
| Surfactant 88% Tween 20 and 12% Tween 80 (Hydrophilic Lipophilic Balance = 16.7) | 25 ml |
| Co-surfactant 95% Ethanol | 21 ml |
| Softeners Lanolin & Stearic acid | q.s. |

EXAMPLE 3

Formulation Trial 3: Each 100 ml Contains (XLP03)

| Name | Composition |
| --- | --- |
| Tea tree oil | 23.7 ml v/v |
| Tulsi oil | 12.0 ml v/v |
| Rose water:Citrus juice in 1:1 ratio | 17.8 ml v/v |
| Surfactant 88% Tween 20 and 12% Tween 80 (Hydrophilic Lipophilic Balance = 16.7) | 25 ml |
| Co-surfactant 95% Ethanol | 21 ml |
| Softeners Lanolin & Stearic acid | q.s. |

EXAMPLE 4

Formulation Trial 4: Each 100 ml Contains (XLP04)

| Name | Composition |
| --- | --- |
| Tea tree oil | 35.7 ml v/v |
| Rose water:Citrus juice in 1:1 ratio | 17.8 ml v/v |
| Surfactant 88% Tween 20 and 12% Tween 80 (Hydrophilic Lipophilic Balance = 16.7) | 25 ml |
| Co-surfactant 95% Ethanol | 21 ml |
| Softeners Lanolin & Stearic acid | q.s. |

EXAMPLE 5

Formulation Trial 5: Each 100 ml Contains (XLP05)

| Name | Composition |
|---|---|
| Tea tree oil | 17.8 ml v/v |
| Tulsi oil | 3.6 ml v/v |
| Rosemary oil | 1.8 ml v/v |
| Lavender oil | 5.4 ml v/v |
| *Mentha* oil | 7.1 ml v/v |
| Rose water:Citrus juice in 1:1 ratio | 17.8 ml v/v |
| Surfactant 88% Tween 20 and 12% Tween 80 (Hydrophilic Lipophilic Balance = 16.7) | 25 ml |
| Co-surfactant 95% Ethanol | 21 ml |
| Softeners | q.s. |
| Lanolin & Stearic acid | |

EXAMPLE 6

Formulation Trial 6: Each 100 ml Contains (XLP06)

| Name | Composition |
|---|---|
| Tea tree oil | 21.4 ml v/v |
| Rosemary oil | 1.8 ml v/v |
| Lavender oil | 5.4 ml v/v |
| *Mentha* oil | 7.1 ml v/v |
| Citrus juice | 17.8 ml v/v |
| Surfactant 88% Tween 20 and 12% Tween 80 (Hydrophilic Lipophilic Balance = 16.7) | 25 ml |
| Co-surfactant 95% Ethanol with extract of *Azarichata indica*, | 21 ml |
| Softeners | q.s. |
| Lanolin & Stearic acid | |

EXAMPLE 7

Formulation Trial 7: Each 100 ml Contains (XLP07)

| Name | Composition 100 ml |
|---|---|
| Tea tree oil | 19.11 ml v/v |
| Rosemary oil | 4.55 ml v/v |
| *Mentha* oil | 0.91 ml v/v |
| Citrus juice | 24.57 ml v/v |
| Surfactant 88% Tween 20 and 12% Tween 80 (Hydrophilic Lipophilic Balance = 16.7) | 30.94 ml |
| Co-surfactant Ethanol | 20 ml |

EXPERIMENT 8

Inhibitory Effect of XLP-07 on Acne and Related Conditions in Humans

| No. of Patients | Category Whiteheads/Blackheads/ Papules/Pustules/ Nodules/Cysts | Age (in years) | Duration of treatment & relief time with XLP-07 | Duration of treatment & relief time with standard Clearasil | Percentage of faster healing with XLP07 over cleasasil |
|---|---|---|---|---|---|
| Patient 1 | Whiteheads | 08 years | — | 3 days | 33.3% |
| Patient 2 | Whiteheads | 10 years | 2 days | — | |
| Patient 3 | Blackheads | 12 years | — | 4 days | 25% |
| Patient 4 | Blackheads | 15 years | 3 days | — | |
| Patient 5 | Papules | 18 years | 5 days | — | 54.5% |
| Patient 6 | Papules | 17.5 years | — | 9 days | |
| Patient 7 | Papules | 27 years | 5 days | — | |
| Patient 8 | Papules | 20 years | — | 13 days | |
| Patient 9 | Pustules | 22 years | 8 days | — | 61.9% |
| Patient 10 | Pustules | 19 years | — | 21 days | |
| Patient 11 | Cysts | 25 years | 10 days | — | 60% |
| Patient 12 | Cysts | 32 years | — | 25 days | |

Observation Criteria: Mild to Moderate acne consists of Whiteheads, Blackheads, Papules & Pustules. Severe acne is characterized by Nodules and Cysts.

Conclusion: XLP07 the product of current invention is significantly more efficacious than Clearesil (the leading brand for acne treatment in India).

EXPERIMENT 9

Microbiological Study of XLP-07 and Its Comparison with the Acne-n-Pimple Cream, (Himalaya & Co.)

XLP-07 vs Acne-n-Pimple Cream

| Microorganism | XLP-07 | Standard Acne-n-Pimple cream |
|---|---|---|
| *S. epidermidis* (MTCC435) (120 µl) | 17.17 ± 1.4 mm | 17.10 ± 1.5 mm |
| *S. epidermidis* (MTCC435) (1:4 dilution) | 11.55 ± 1.3 mm | Nil |

-continued

| Microorganism | XLP-07 | Standard Acne-n-Pimple cream |
|---|---|---|
| S. aureus (MTCC 737) (100 µl) | 16.90 ± 1.2 mm | 16.27 ± 1.4 mm |
| S. aureus (MTCC 737) (1:3 dilution) | 11.88 ± 1.0 mm clear zone | Intermediate zone with dense growth |

Conclusion

1 Zone of inhibition against *S. epidermidis* & *S. aureus* was more in XLP-07 as compared to the standard Acne-n-Pimple cream.

2 XLP-07 has been found to be more effective even at very low concentrations there by indicating sustained release effect of therapeutically active agent having strong bactericidal activity.

XLP-07 vs Clearasil

| Microorganism | XLP-07 | Clearasil |
|---|---|---|
| S. epidermidis (MTCC435) (18 µl) | 9.29 mm clear zone | Nil |
| S. aureus (MTCC737) (18 µl) | 12.58 mm clear zone | 8.86 mm not clear zone |

Conclusion

1 XLP-07 has been found to be more effective even at low concentration where as the inhibition zone in Clearasil, was either absent or not prominent. Thereby indicating that XLP07 has superior bactericidal activity against said pathogens.

EXPERIMENT 10

Screening of Individual Oil for Efficacy

| Ingredient | S. aureus (MTCC 737) | S. epidermidis (MTCC435) |
|---|---|---|
| Tea tree oil | 10 mm | 13 mm |
| Rosemary oil | 7.5 mm | 12.6 mm |
| Lavender oil | 0 | not clear |
| Basil oil | 0 | not clear |
| *Mentha* oil | 0 | 7.8 mm |
| Rose + Lemon juice | 12.5 mm | 12.6 mm |
| Freshly squeezed Lemon Juice | 14 mm | 16 mm |

EXPERIMENT 11

Different Hydrophilic-Lipophilic Balance (HLB) Trials

| HLB 4 | HLB 14 | HLB 15.51 | HLB 15.85 | HLB 16 | HLB 16.33 | HLB 16.4 | HLB 16.7 (Final) |
|---|---|---|---|---|---|---|---|
| 83% | 9% | 30% | 50% | 60% | 78% | 85% | 88% |
| Span 80 | Span 80 | Tween 20 | Tween 20 | Tween 20 | Tween 20 | Tween 20 | Tween 20 |
| 17% | 91% | 70% | 50% | 40% | 22% | 15% | 12% |
| Tween 80 | Tween 80 | Tween 80 | Tween 80 | Tween 80 | Tween 80 | Tween 80 | Tween 80 |
| Trial was not successful | Trial was not successful | Trial was successful | Trial was successful | Trial was successful | Trial was successful | Trial was successful | Trial was successful |

EXPERIMENT 12

Comparative Study of Anti Oxidant and Anti Inflammatory Enzyme Levels and Related Biochemical Parameters in Acne Induced Rat Model Acne was induced in rats which were then divided in 3 groups. Control untreated infected group I, group II was treated with Clearasil and group III was treated with XLP07 for a period of 7 days. Different biochemical parameters were studied in all the groups after 7 days. Refer FIGS. 3 and 4.

Figure 3:
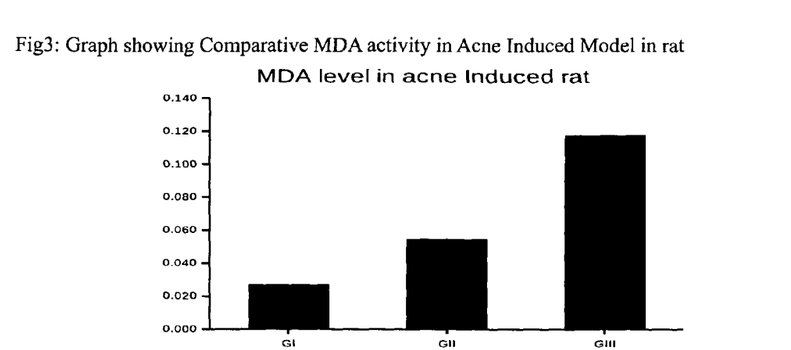
FIG. 3: Graph showing significant increase in MDA activity of group III as compared to G-II and G-I.

Conclusion: FIG. 3: indicates drastic increase in MDA activity in Group III after treatment with XLP07 as compared to Group II of Clearasil (a leading acne treatment product in Indian market) and control infected untreated group I. This indicates that XLP07 has better anti oxidant activity as compared to Clearasil.

FIG. 4: indicates drastic decrease in Myeloperoxidase enzyme activity in Group III after treatment with XLP07 as compared to Group II of Clearasil (a leading acne treatment product in Indian market) and control infected untreated group I. This indicates that XLP07 has better anti inflammatory activity as compared to Clearasil.

EXPERIMENT 13

Long Term Stability Data of XLP07

Long Term Stability Data

| PRODUCT: | XLP-07 for External application 5 ml vial | |
|---|---|---|
| Batch No.: | RD/XLP-07/B01 | |
| Date of Mfg.: | February 2006 | Date of Exp.: January 2008 |
| Date of initiating: | Dec. 02, 2006 | Batch Size: 100 vials |
| Packaging: | Filled in 5 ml plastic vials | Test conditions: 30° C. ± 2° C./65% ± 5% RH |
| Storage conditions: | Below 30° C. | |

| | | Specific | | | Refractive | | | Assay (By GC) | | | | |
|---|---|---|---|---|---|---|---|---|---|---|---|---|
| Period (months) | Description | gravity (0.95-1.50 gm/ml) | pH (3.5-5.5) | Viscosity (at 100 rpm) (NMT 50) | Index (1.250 to 1.400) | Ascorbic acid (NLT 50 mg/100 g) | Citric acid (NLT 30 mg/100 g) | Alpha-pinene NLT 0.75% | Gama-terpinene NLT 4.0% | Camphor NLT 0.75% | Terpinene-4-ol NLT 1.0% | Menthol NLT 0.50% |
| Initial | Clear, transparent light golden yellow viscous liquid | 1.04 | 4.21 | 38.7 | 1.338 | 90 | 45 | 1.12% | 4.79% | 1.28% | 1.89% | 0.88% |
| 3 | Clear, transparent light golden yellow viscous liquid | 1.02 | 4.20 | 38.9 | 1.338 | 88 | 44 | 1.10% | 4.75% | 1.23% | 1.87% | 0.85% |
| 6 | Clear, transparent light golden yellow viscous liquid | 1.04 | 4.18 | 39.2 | 1.339 | 87 | 42 | 1.07% | 4.74% | 1.20% | 1.83% | 0.83% |
| 9 | Clear, transparent light golden yellow viscous liquid | 1.04 | 4.18 | 39.2 | 1.339 | 85 | 41 | 1.04% | 4.72% | 1.19% | 1.78% | 0.82% |
| 12 | Clear, transparent light golden yellow viscous liquid | 1.05 | 4.17 | 39.4 | 1.341 | 84 | 40 | 1.02% | 4.70% | 1.16% | 1.75% | 0.80% |
| 18 | Clear, transparent light golden yellow viscous liquid | 1.06 | 4.15 | 39.5 | 1.341 | 82 | 40 | 0.98% | 4.66% | 1.12% | 1.73% | 0.77% |
| 24 | Clear, transparent light golden yellow viscous liquid | 1.06 | 4.15 | 39.5 | 1.341 | 80 | 38 | 0.95% | 4.60% | 1.07% | 1.69% | 0.71% |

REMARKS: 1. All procedure carried out as per STP.
2. Above result shows that product is stable at 30° C. ± 2° C./65% ± 5% RH for 24 months.

Above disclosure describe a manner and method of making the invention and sets forth the best mode contemplated by the inventor for carrying out his invention but is not to be construed as limiting. Various modifications and variations of the described method and system of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications and equivalents of the described modes for carrying out the invention that are obvious to those skilled in formulation development or related fields are intended to be within the scope of the invention.

BRIEF DESCRIPTION OF DRAWINGS

FIG. 1: Graph showing Zeta potential of Nano-emulsion (Experiment 7) where the Zeta potential is −0.0326.

FIG. 2: Graph showing Particle size distribution and Poly Dispersity Index of Nano-emulsion (Experiment 7) where the maximum number of particles are in the range of 0.5 nano meter in diameter.

FIG. 4: Graph showing significant decrease in MPO activity of group III as compared to G-II and G-I.

We claim:

1. A topical herbal nano-emulsion formulation for treatment of acne and other skin disorders, said formulation comprising:
    a medicated aqueous phase comprises at least one or both of a rose water or lemon juice;
    an oil phase comprises at least one essential oil selected from the group consisting of tea tree oil, tulsi oil, rosemary oil, lavender oil, jojoba oil, bergamot oil, clove oil and mentha oil; and at least one non-ionic surfactant and at least one co-surfactant, wherein said medicated aqueous phase is entrapped into a lipid layer of at least one essential oil; wherein a ratio of said medicated aqueous phase and said oil phase is in the range of 1:1 to 1:2; and wherein said topical herbal nano-emulsion formulation has a particle size of ≦5 nm.

2. The topical herbal nano-emulsion formulation of claim 1,
wherein said non-ionic surfactant and said co-surfactant are present in a ratio of 1.5:1 to 1:1.5; and
wherein said co-surfactant is a short and medium chain alcohol.

3. The topical herbal nano-emulsion formulation of claim 1,
wherein a ratio of said rose water and said lemon juice is in the range of 1:1; and
wherein said topical herbal nano-emulsion formulation has a polydispersity index of ≦0.200 and a zeta potential of ≦−0.0500.

4. The topical herbal nano-emulsion formulation of claim 1,
wherein said non-ionic surfactant is selected from the group consisting of polyoxyethylene sorbitan fatty acid esters, Tween-80, Tween-20, polyethylene glycols, polyoxyethylene stearates, colloidal silicon dioxide, phosphates, sodium dodecyl sulfate, calcium carboxymethyl cellulose, sodium carboxymethyl cellulose, methyl cellulose, hydroxyethyl cellulose, hydroxypropyl cellulose, hydroxypropylmethyl cellulose phthalate, microcrystalline cellulose, magnesium aluminum silicate, triethanolamine, polyvinyl alcohol, and polyvinylpyrrolidone;
wherein said non-ionic surfactant is at least one of a Tween-80, at least one of a Tween-20; and
wherein a ratio of Tween-80:Tween-20 is 70:30, 80:20, or 88:12.

5. The topical herbal nano-emulsion formulation of claim 1,
wherein said co-surfactant is an ethanol.

6. The topical herbal nano-emulsion formulation of claim 1,
wherein said lemon juice comprises freshly squeezed lemon juice;
wherein said freshly squeezed lemon juice comprises 25±5% of said medicated aqueous phase;
wherein said essential oil comprises in volume/volume range, said tea tree oil as 20±5%, said rosemary oil as 5±5%, and said mentha oil as 1.0±5% ;
wherein said non-ionic surfactant comprises in volume/volume ratio Tween-20:Tween-80 as 88:12;
wherein a ratio of non-surfactant to co-surfactant is 1.5:1 with HLB value of 16.7; and wherein said topical herbal nano-emulsion formulation has a ratio of medicated aqueous phase:oil phase as 1:1 and particle size of ≦0.5 nm, zeta potential is ≦−0.0326 and polydispersity index is ≦0.169.

7. The topical herbal nano-emulsion formulation of claim 1,
wherein said rose water and said lemon juice in a ratio of 1:1 available in the range of 18±5% as said medicated aqueous phase;
wherein said medicated aqueous phase is entrapped in volume/volume range of said essential oil comprising 18±5% of tea tree oil, 4±5% of tulsi oil, 2±5% of rosemary oil, 5±5% of lavender oil and 7±5% of mentha oil, together as said oil phase entrapping said medicated aqueous phase;
wherein the ratio of medicated aqueous phase:oil phase is 1:2;
wherein said non-ionic surfactant with volume/volume ratio of Tween-20:Tween-80 is 88:12;
wherein said co-surfactant is ethanol and a ratio of said non-ionic surfactant to said co-surfactant is 1.2:1 with HLB value of 16.7; and
wherein said topical herbal nano-emulsion formulation has, a zeta potential ≦−0.0500 and a polydispersity index ≦0.200.

8. A method of preparing the topical herbal nano-emulsion formulation according to claim 1, said method comprising the steps of:
providing a medicated aqueous phase comprises at least one or both of a rose water or lemon juice;
providing an oil phase comprises at least one essential oil selected from the group consisting of tea tree oil, tulsi oil, rosemary oil, lavender oil, jojoba oil, bergamot oil, clove oil and mentha oil;
wherein said medicated aqueous phase is entrapped into a lipid layer of at least one essential oil; wherein a ratio of said medicated aqueous phase and said oil phase is in the range of 1:1 to 1:2;
providing at least one non-ionic surfactant and at least one co-surfactant;
providing ethanol as co-surfactant;
mixing said medicated aqueous phase and oil phase to form a mixture A;
emulsifying mixture A with said at least one non-ionic surfactant to obtain a macro-emulsion; and
mixing ethanol with said macro-emulsion to form a topical herbal nano-emulsion formulation having a particle size of ≦5 nm.

9. The method of claim 8, further comprising adding a softener.

* * * * *